United States Patent
Homoto et al.

[11] Patent Number: 5,849,963
[45] Date of Patent: Dec. 15, 1998

[54] METHOD FOR PRODUCING DIFLUOROMETHANE AND 1,1,1,2-TETRAFLUOROETHANE

[75] Inventors: Yukio Homoto; Kunitada Tanaka; Takashi Shibanuma; Satoshi Komatsu; Satoshi Koyama, all of Osaka, Japan

[73] Assignee: Daikin Industries, Ltd., Osaka, Japan

[21] Appl. No.: 656,229

[22] PCT Filed: Dec. 9, 1994

[86] PCT No.: PCT/JP94/02070

§ 371 Date: Jun. 7, 1996

§ 102(e) Date: Jun. 7, 1996

[87] PCT Pub. No.: WO95/15937

PCT Pub. Date: Jun. 15, 1995

[30] Foreign Application Priority Data

Dec. 9, 1993 [JP] Japan .................... 5-309523

[51] Int. Cl.[6] .......... C07C 17/158; C07C 17/20; C07C 17/06
[52] U.S. Cl. .......... 570/466; 570/168; 570/169; 570/170
[58] Field of Search .................... 570/166, 168, 570/169, 170

[56] References Cited

U.S. PATENT DOCUMENTS 2,749,373  6/1956  Meyer .................... 570/256

FOREIGN PATENT DOCUMENTS

| 0128510 | 12/1984 | European Pat. Off. |
| 423004 | 2/1942 | Japan. |
| 03-294237 | 12/1991 | Japan. |
| 07-017882 | 1/1995 | Japan. |
| WO93 16798 | 9/1993 | WIPO. |
| WO9325505 | 12/1993 | WIPO. |

OTHER PUBLICATIONS

"Chemistry and Industry of Fluorine Compound", p. 267, published Dec. 1977.

*Primary Examiner*—Alan L. Rotman
*Attorney, Agent, or Firm*—Birch, Stewart, Kolasch & Birch, LLP

[57] ABSTRACT

According to the method for producing difluoromethane and 1,1,1,2-tetrafluoroethane, having the steps of:

(1) reacting methylene chloride and 1,1,2-trichloroethylene with hydrogen fluoride in a vapor phase In the presence of a fluorinating catalyst and 1,1,1,2-tetrafluoroethane in a first reactor; and (2) reacting 1,1,1-trifluorochloroethane with hydrogen fluoride in a vapor phase in the presence of a fluorinating catalyst in a second reactor, and supplying the reaction mixture from the second reactor to the first reactor, HFC-32 can be obtained in high conversion and high selectivity by fluorinating HCC-30 using commonly a large (excess) amount of HF which is required for producing HFC-134a.

14 Claims, 3 Drawing Sheets

5,849,963

METHOD FOR PRODUCING DIFLUOROMETHANE AND 1,1,1,2-TETRAFLUOROETHANE

CROSS REFERNCE

This application is a 371 of PCT/IP94/02070 filed Dec. 09, 1994.

FIELD OF THE INVENTION

The present invention relates to a method for producing difluoromethane and 1,1,1,2-tetrafluoroethane. Difluoromethane and 1,1,1,2-tetrafluoroethane are alternative fluorocarbons, and are useful as a cooling medium and the like.

DESCRIPTION OF RELATED ART

As the method for producing difluoromethane ($CH_2F_2$, HFC-32), a liquid phase synthesis process (cf. U.S. Pat. No. 2,749,373) and vapor phase synthesis process (cf. Japanese Patent Publication Nos. 3004/1967 and 2251321/1984) comprising using methylene chloride ($CH_2Cl_2$, HCC-30) as a raw material are known.

It is a known fact that it is difficult to react methylene chloride in good conversion according to the vapor phase synthesis process (cf. "Chemistry and Industry of Fluorine Compound", page 267, published on December 1977 and Japanese Patent Publication No. 3004/1967). It is possible to increase the conversion of methylene chloride by using excess HF relative to methylene chloride. However, a large amount of HF must be disposed or recovered and, therefore, an economical disadvantage arises (cf. Japanese Patent Kokai Publication No. 2251321/1984).

Japanese Patent Kokai Publication No. 2942371/1991 discloses a process comprising reacting 1,1,1-trifluorochloroethane (HCFC-133a) with HF to obtain 1,1,1,2-tetrafluoroethane (HFC-134a), adding 1,1,2-trichloroethylene (HCC-1120) to a crude reaction gas to conduct the reaction from HCC-1120 into HCFC-133a in another reactor without exerting an influence on the other gas and recycling the formed 133a and a HF, as a process for producing efficiently 1,1,1-trifluorochloroethane (HCFC-133a) and 1,1,1,2-tetrafluoroethane (HFC-134a).

The conversion reaction from HCC-1120 into HCFC-133a is a largely exothermic reaction, and it is suggested that the prevention of a heat spot formation in a catalyst layer by the reaction is useful to prolong the catalytic life.

SUMMARY OF THE INVENTION

An object of the present invention is to provide a method for effectively and simultaneously producing difluoromethane and 1,1,1,2-tetrafluoroethane in one apparatus.

The present invention provides a method for producing difluoromethane and 1,1,1,2-tetrafluoroethane, comprising the steps of:

(1) reacting methylene chloride with hydrogen fluoride in a vapor phase at a reaction temperature of 180° to 320° C. in the presence of a fluorinating catalyst and 1,1,1,2-tetrafluoroethane to give difluoromethane, and reacting 1,1,2-trichloroethylene with hydrogen fluoride to give 1,1,1-trifluorochloroethane, in a first reactor, (2) reacting 1,1,1-trifluorochloroethane with hydrogen fluoride in a vapor phase at a reaction temperature of 280° to 400° C., which is higher than the reaction temperature of the first reactor, in the presence of a fluorinating catalyst to give 1,1,1,2-tetrafluoroethane in a second reactor, and supplying the reaction mixture from the second reactor to the first reactor;

(3) recovering difluoromethane, 1,1,1,2-tetrafluoroethane and hydrogen chloride from the reaction mixture of the first reactor; and (4) supplying the remainder of the reaction mixture containing 1,1,1-trifluorochloroethane from the first reactor to the second reactor after recovering in the step (3).

In addition, the present invention provides a method for producing difluoromethane and 1,1,1,2-tetrafluoroethane, comprising the steps of:

(1) reacting methylene chloride with hydrogen fluoride in a vapor phase at a reaction temperature of 180° to 320° C. in the presence of a fluorinating catalyst and 1,1,1,2-tetrafluoroethane to give difluoromethane, and reacting 1,1,2-trichloroethylene with hydrogen fluoride to give 1,1,1-trifluorochloroethane, in a first reactor, (2) reacting 1,1,1-trifluorochloroethane with hydrogen fluoride in a vapor phase at a reaction temperature of 280° to 400° C. which is higher than the reaction temperature of the first reactor in the presence of a fluorinating catalyst to give 1,1,1,2-tetrafluoroethane in a second reactor, and supplying the reaction mixture from the second reactor to the first reactor;

(3) reacting the reaction mixture from the first reactor with hydrogen fluoride in a vapor phase at a reaction temperature of 150° to 240° C., which is lower than the reaction temperature of the first reactor, in the presence of a fluorinating catalyst to reduce an amount of methylene chloride existing in the reaction mixture, in a third reactor;

(4) recovering difluoromethane, 1,1,1,2-tetrafluoroethane and hydrogen chloride from the reaction mixture of the third reactor; and (5) supplying the remainder of the reaction mixture containing 1,1,1-trifluorochloroethane from the third reactor to the second reactor after recovering in the step (4).

Further, the present invention provides a method for producing difluoromethane and 1,1,1,2-tetrafluoroethane, comprising the steps of:

(1) reacting methylene chloride with hydrogen fluoride in a vapor phase at a reaction temperature of 180° to 320° C. in the presence of a fluorinating catalyst and 1,1,1,2-tetrafluoroethane to give difluoromethane, and reacting 1,1,2-trichloroethylene with hydrogen fluoride to give 1,1,1-trifluorochloroethane, in a first reactor;

(2) reacting 1,1,1-trifluorochloroethane with hydrogen fluoride in a vapor phase at a reaction temperature of 280° to 400° C., which is higher than the reaction temperature of the first reactor, in the presence of a fluorinating catalyst to give 1,1,1,2-tetrafluoroethane in a second reactor, and supplying the reaction mixture from the second reactor to the first reactor;

(3) reacting the reaction mixture from the first reactor with hydrogen fluoride in a vapor phase at a reaction temperature of 150° to 240° C., which is lower than the reaction temperature of the first reactor, in the presence of a fluorinating catalyst to reduce an amount of methylene chloride existing in the reaction mixture, in a third reactor;

(4) reacting the reaction mixture from the third reactor with hydrogen fluoride in a vapor phase at 100° to 190° C., which is lower than te reaction temperature of the third reactor, in the presence of a fluorinating catalyst, in at least one fourth reactor;

(5) recovering difluoromethane, 1,1,1,2-tetrafluoroethane and hydrogen chloride from the reaction mixture from the fourth reactor; and (6) supplying the remainder of the reaction mixture containing 1,1,1-trifluorochloroethane from the fourth reactor to the second reactor after recovering in the step (5).

The present invention further provides a method for producing difluoromethane and 1,1,1,2-tetrafluoroethane, comprising the steps of:

(1) reacting methylene chloride with hydrogen fluoride in a vapor phase at a reaction temperature of 180° to 320° C. in the presence of a fluorinating catalyst and 1,1,1,2-tetrafluoroethane to give difluoromethane, and reacting 1,1,2-trichloroethylene with hydrogen fluoride to give 1,1,1-trifluorochloroethane, in a first reactor;

(2) reacting 1,1,1-trifluorochloroethane with hydrogen fluoride in a vapor phase at a reaction temperature of 280° to 400° C., which is higher than the reaction temperature of the first reactor, in the presence of a fluorinating catalyst to give 1,1,1,2-tetrafluoroethane in a second reactor, and supplying the reaction mixture from the second reactor to the first reactor;

(3) recovering difluoromethane, 1,1,1,2-tetrafluoroethane and hydrogen chloride from the reaction mixture of the first reactor; and (4) reacting the remainder of the reaction mixture containing 1,1,1-trifluorochloroethane from the first reactor with hydrogen fluoride in a vapor phase at a temperature of 170° to 320° C. in the presence of a fluorinating catalyst in a fifth reactor after recovering in the step (3), and supplying the reaction mixture from the fifth reactor to the second reactor.

The present invention further provides a method for producing difluoromethane and 1,1,1,2-tetrafluoroethane, comprising the steps of:

(1) reacting methylene chloride with hydrogen fluoride in a vapor phase at a reaction temperature of 180° to 320° C. in the presence of a fluorinating catalyst and 1,1,1,2-tetrafluoroethane to give difluoromethane, and reacting 1,1,2-trichloroethylene with hydrogen fluoride to give 1,1,1,-trifluorochloroethane, in a first reactor;

(2) reacting 1,1,1-trifluorochloroethane with hydrogen fluoride in a vapor phase at a reaction temperature of 280° to 400° C., which is higher than the reaction temperature of the first reactor, in the presence of a fluorinating catalyst to give 1,1,1,2-tetrafluoroethane in a second reactor, and supplying the reaction mixture from the second reactor to the first reactor;

(3) reacting the reaction mixture from the first reactor with hydrogen fluoride in a vapor phase at 150° to 240° C., which is lower than the reaction temperature of the first reactor, in the presence of a fluorinating catalyst to reduce an amount of methylene chloride existing in the reaction mixture, in a third reactor;

(4) recovering difluoromethane, 1,1,1,2-tetrafluoroethane and hydrogen chloride from the reaction mixture of the third reactor; and (5) reacting the remainder of the reaction mixture containing 1,1,1-trifluorochloroethane from the third reactor with hydrogen fluoride in a vapor phase at a temperature of 170° to 320° C. in the presence of a fluorinating catalyst in a fifth reactor after recovering in the step (4), and supplying the reaction mixture from the fifth reactor to the second reactor.

The present invention further provides a method for producing difluoromethane and 1,1,1,2-tetrafluoroethane, comprising the steps of:

(1) reacting methylene chloride with hydrogen fluoride in a vapor phase at a reaction temperature of 180° to 320° C. in the presence of a fluorinating catalyst and 1,1,1,2-tetrafluoroethane to give difluoromethane, and reacting 1,1,2-trichloroethylene with hydrogen fluoride to give 1,1,1-trifluorochloroethane, in a first reactor;

(2) reacting 1,1,1-trifluorochloroethane with hydrogen fluoride in a vapor phase at a reaction temperature of 280° to 400° C., which is higher than the reaction temperature of the first reactor, in the presence of a fluorinating catalyst to give 1,1,1,2-tetrafluoroethane in a second reactor, and supplying the reaction mixture from the second reactor to the first reactor;

(3) reacting the reaction mixture from the first reactor with hydrogen fluoride in a vapor phase at 150° to 240° C., which is lower than the reaction temperature of the first reactor, in the presence of a fluorinating catalyst to reduce an amount of methylene chloride existing in the reaction mixture, in a third reactor;

(4) reacting the reaction mixture from the third reactor with hydrogen fluoride in a vapor phase at 100° to 190° C., which is lower than the reaction temperature of the third reactor, in the presence of a fluorinating catalyst, in at least one fourth reactor;

(5) recovering difluoromethane, 1,1,1,2-tetrafluoroethane and hydrogen chloride from the reaction mixture of the fourth reactor; and (6) reacting the remainder of the reaction mixture containing 1,1,1-trifluorochoroethane from the fourth reactor with hydrogen fluoride in a vapor phase at a temperature of 170° to 320° C. in the presence of a fluorinating catalyst in a fifth reactor after recovering in the step (5), and supplying the reaction mixture from the fifth reactor to the second reactor.

DETAILED DESCRIPTION OF THE INVENTION

In the present invention, it is preferred to recover the unreacted methylene chloride (HCC-30) and/or chlorofluoromethane (HCFC-31, $CH_2FCl$) existing in the reaction mixture obtained from (a) the first reactor when no third reactor exists, (b) the third reactor when the first and third reactors exist or (c) the fourth reactor when the first, third and fourth reactor exists, and to recycle the recovered HCC-30 and/or HCFC-31 to the first or third reactor. These gases can be recovered from the reaction mixture by operations such as an extraction, a two phase separation, a fractional distillation, etc. When the reaction mixture is fed to the second reactor without recovering HCC-30 and HCFC-31, the following reactions can arise in the second reactor.

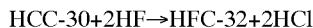
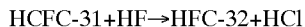

It is supposed that the resultant HCl decreases the conversion from HCFC-133a into HFC-134a. However, a decrease in conversion becomes small by decreasing the amount of the unreacted HCC-30 and HCFC-31 which are fed to the second reactor, so that the production efficiency of HFC-134a is increased.

The method of the present invention uses
(a) the first and second reactors,
(b) the first to third reactors,
(c) the first to fourth reactors,
(d) the first, second and fifth reactors,
(e) the first, second, third and fifth reactors, or
(f) the first to fifth reactors.

Figure 1:
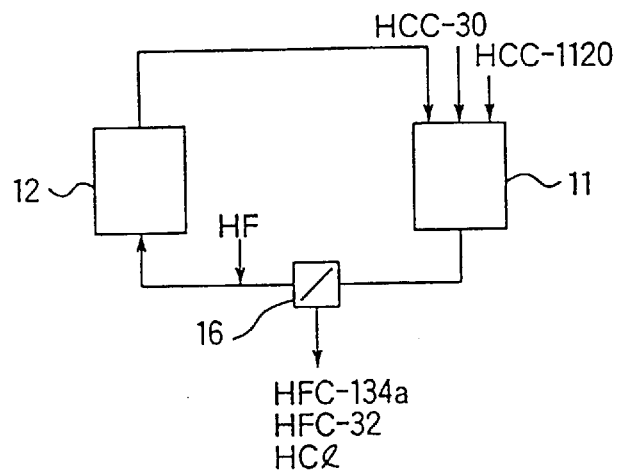
FIG. 1 is a schematic view illustrating an apparatus for conducting the method of the present invention using first and second reactors.

FIG. 1 is a schematic diagram illustrating an apparatus for conducting the method of the present invention using first and second reactors. This apparatus has a first reactor 11, a second reactor 12, and a separator 16 for recovering HFC-134a, HFC-32 and hydrogen chloride.

Figure 2:
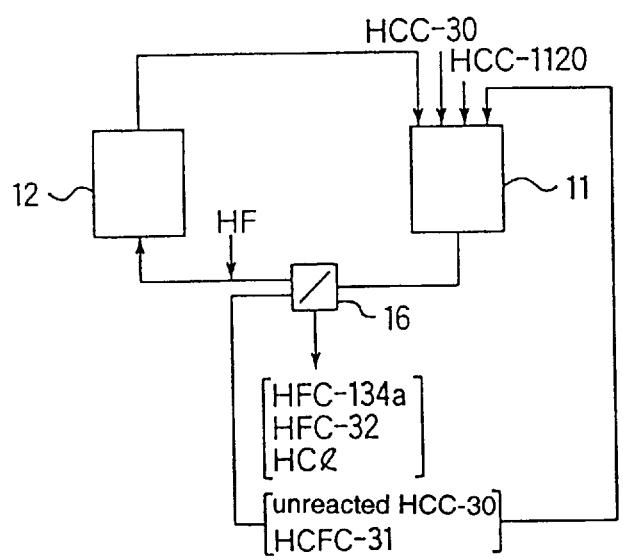
FIG. 2 is a schematic view illustrating another embodiment of an apparatus for conducting the method of the present invention using first and second reactors.

FIG. 2 is a schematic diagram illustrating another embodiment of an apparatus for conducting the method of the present invention using first and second reactors. In this apparatus, the unreacted HCC-30 and/or HCFC-31 in the mixture obtained from the first reactor 11 are separated, and then the unreacted HCC-30 and/or HCFC-31 are supplied to the first reactor 11.

Figure 3:
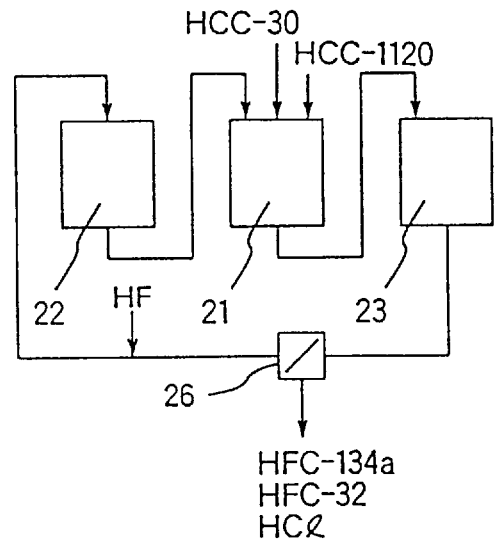
FIG. 3 is a schematic view illustrating an apparatus for conducting the method of the present invention using first to third reactors.

FIG. 3 is a schematic diagram illustrating an apparatus for conducting the method of the present invention using first to third reactors. This apparatus has a first reactor 21, a second reactor 22, a third reactor 23, and a separator 26 for recovering HFC-134a, HFC-32 and hydrogen chloride.

Figure 4:
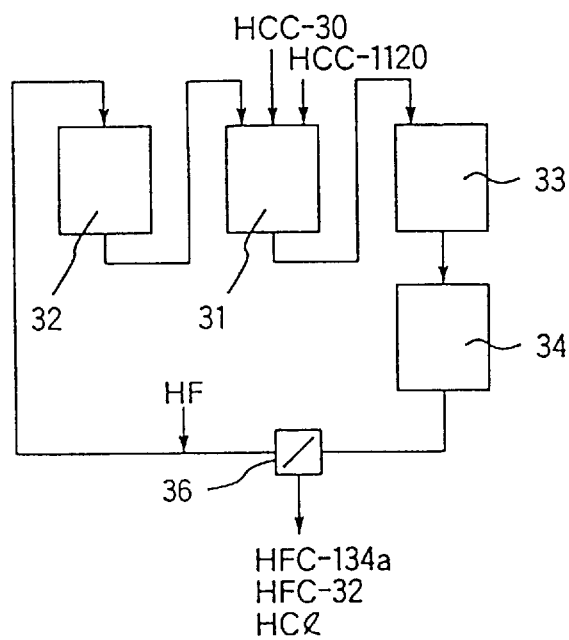
FIG. 4 is a schematic view illustrating an apparatus for conducting the method of the present invention using first to fourth reactors.

FIG. 4 is a schematic diagram illustrating an apparatus for conducting the method of the present invention using first to fourth reactors. This apparatus has a first reactor 31, a second reactor 32, a third reactor 33, a fourth reactor 34, and a separator 36 for recovering HFC-134a, HFC-32 and hydrogen chloride.

Figure 5:
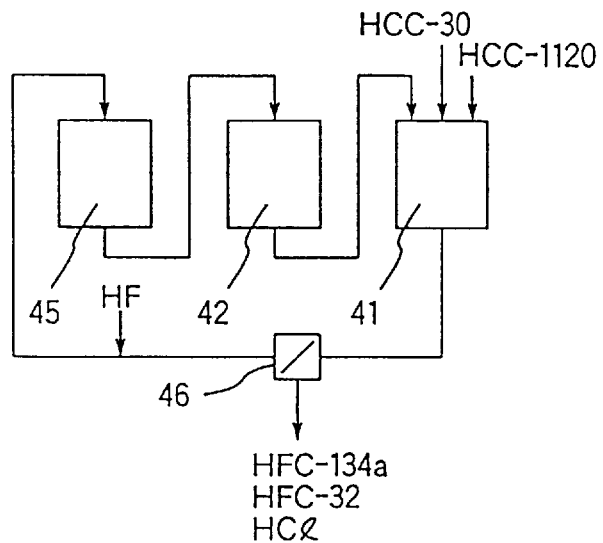
FIG. 5 is a schematic view illustrating an apparatus for conducting the method of the present invention using first, second and fifth reactors.

FIG. 5 is a schematic diagram illustrating an apparatus for conducting the method of the present invention using first, second and fifth reactors. This apparatus has a first reactor 41, a second reactor 42, a fifth reactor 45 and a separator 46 for recovering HFC-134a, HFC-32 and hydrogen chloride.

Figure 6:
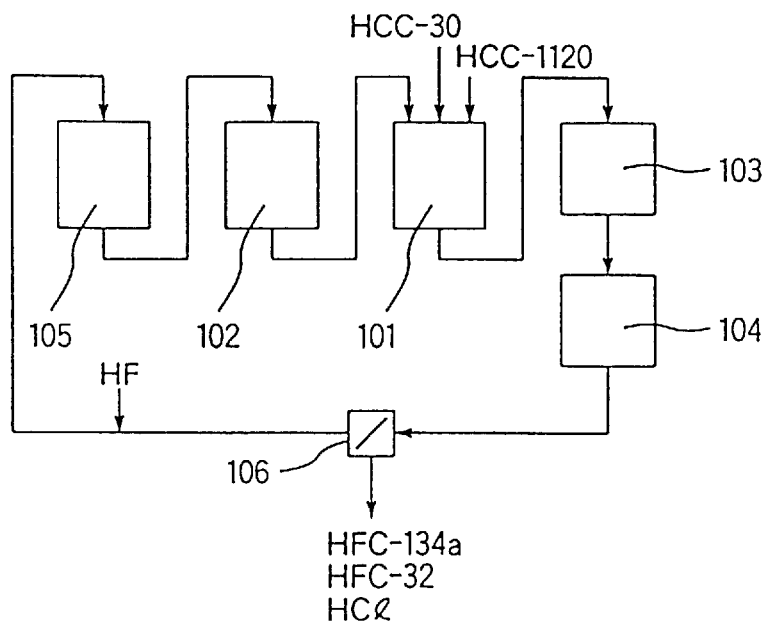
FIG. 6 is a schematic view illustrating an apparatus for conducting the method of the present invention using first to fifth reactors.

FIG. 6 is a schematic diagram illustrating a apparatus for conducting the method of the present invention using first to fifth reactors. This apparatus has a first reactor 101, a second reactor 102, a third reactor 103, a fourth reactor 104, a fifth reactor 105, and a separator 106 for recovering HFC-134a, HFC-32 and hydrogen chloride. It is also possible to use an embodiment wherein no fourth reactor 104 exists.

In the first reactor, methylene chloride (HCC-30) is reacted with hydrogen fluoride in a vapor phase at a reaction temperature of 180° to 320° C. in the presence of a fluorinating catalyst and 1,1,1,2-tetrafluoroethane (HFC-134a) to give difluoromethane (HFC-32), and then 1,1,2-trichloroethylene (HCC-1120) is reacted with hydrogen fluoride to give 1,1,1-trifluorochloroethane (HCFC-133a).

HFC-134a acts as a diluting agent for reducing a concentration of HCC-1120 and hydrogen fluoride.

In the first reactor, the following reactions arise.

 (1)

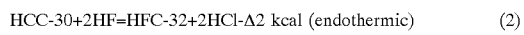 (2)

It is also possible that the following reaction arises.

 (3)

HCl is generated according to the formula (1) and (2). It is supposed that the generated HCl gives an adverse influence on HFC-134a formation because ΔG (Gibbs energy) of the reaction from HCFC-133a into HFC-134a is smaller than that of the formula (1). In the present invention, however, the actual conversion from HFC-134a into HCFC-133a is smaller than an expected value derived from a relationship of the equilibrium constant and the concentration of the raw material and the resulting system. Accordingly, it is possible to produce efficiently HCFC-133a and HCFC-32 without disadvantageous reaction from HFC-134a into HCFC-133a. The exothermic reaction (formula (1)) and the endothermic reaction (formula (2)) are combined and, therefore, the efficiency of energy is good and it contributes to prevent the formation of heat spot in the reactor.

In the first reactor, HCFC-133a and HFC-32 can be produced efficiently. Since HFC-134a acts as a diluting agent for reducing the concentration of HCC-1120 and HF which are the raw material, the control of the reaction heat becomes easier and more efficient. Similarly, an excess amount of HF reduces the concentration product of HCC-1120 and HF and acts as a heat remover and, therefore, the control of the reaction heat becomes easy. In the first reactor, the amount of 1,1-dichloro-2,2-difluoroethylene (CFC-1122) is also reduced (CFC-1122+HF→HCFC-133a).

Since the reaction (HCC-30+2HF→HFC-32+2HCl) in the first reactor can proceed in the presence of excess HF, the good conversion can be obtained. In this reaction, while the amount of HF may be stoichiometrically two equivalents, an excess amount of HF can give higher conversion. In a system where a single reaction (the conversion from HCC-30) is conducted, there is a limitation of using the excess amount of HF in view of the cost of the apparatus. In a system which also include a reaction from HCC-1120, the stoichiometrically excess amount of HF is required in the second reactor, and the amount of HF can be easily set to an excess amount so as to supply the reaction mixture from the second reactor to the first reactor. This is advantageous for simultaneous production.

The reaction temperature of the first reactor is usually from 180° to 320° C., preferably from 200° to 300° C., more preferably from 230° to 270° C. When it is lower than 180° C., the conversion of HCC-1120 is lowered. When it is higher than 320° C., the catalyst is remarkably deteriorated and an amount of HFC-134a decreases. The contact time is usually from 0.5 to 60 seconds, preferably from 2 to 10 seconds. The reaction pressure is not specifically limited unless the raw material and product are liquefied. The reaction pressure is usually from 1 to 20 atm, preferably from 1 to 10 atm, in view of simplification, economy, etc. In the first reactor, a fluorinating catalyst is usually used, but its type and production method are not specifically limited. Examples of the fluorinating catalyst include fluorinated chromium oxide obtained by fluorinating a heat-treated hydrate of chromium (III) hydroxide with hydrogen fluoride; chromium (III) trifluoride; fluorinated aluminum oxide obtained by fluorinating aluminum oxide with hydrogen fluoride; catalyst obtained by supporting at least one element selected from Ti, V, Zr, Mo, Ge, Sn and Pb on alumina, fluorinated alumina or partially fluorinated alumina; etc.

The raw material supplied to the first reactor may be HCC-1120, HCC-30 and HF, and contains HFC-134a. It may also contain compounds such as hydrogen chloride (HCl), HCFC-133a, 1,1-dichloro-2,2-difluoroethylene (CFC-1122), etc.

In the raw material supplied to the first reactor, a molar ratio of HCC-1120 to HCC-30 is not specifically limited, but is usually from 10:1 to 1:2, preferably from 5:1 to 1:1. In the first reactor, the amount in mole of HF is usually from 1 to 50 times, preferably from 2 to 20 times, based on the total value of a 3-fold value of the mole amount of 1,1,2-trichloroethylene and 2-fold value of mole amount of methylene chloride. The amount of HFC-134a is usually from 0.2 to 5 mol (e.g. about equimol) per 1 mol of HCC-1120.

In the second reactor, 1,1,1-trifluorochloroethane (HCFC-133a) is reacted with hydrogen fluoride in a vapor phase at a reaction temperature of 280° to 400° C., which is higher than the reaction temperature of the first reactor, in the presence of a fluorinating catalyst to produce 1,1,1,2-tetrafluoroethane (HFC-134a). The reaction temperature is usually from 280° to 400° C., preferably from 290° to 350° C. When the temperature is lower than 280° C., the amount of the generated HFC-134a is lowered. When the temperature is higher than 400° C., the deterfiFaion of the catalyst is remarkable. The temperature of the first reactor is set at a temperature lower than that of the second reactor. For example, a difference between the temperatures of the first and second reactors is from 30° to 120° C. The reaction pressure is usually from 1 to 20 atm, preferably from 1 to 10 atm. The contact time is usually from 0.5 to 60 seconds, preferably from 2 to 10 seconds. Examples of the fluorinating catalyst are the same as those described in the first reactor. The amount of hydrogen fluoride is usually from 0.9 to 15 mol, preferably from 3 to 6 mol, based on 1 mol of HCFC-133a. The raw material supplied to the second reactor contains HCFC-133a and HF, and it may contain trichloroethylene, HCFC-132b ($CF_2ClCHCl_2$), HCFC-124 ($CF_3CFHCl$), etc.

In the third reactor, the reaction mixture obtained from the first reactor is reacted with hydrogen fluoride in a vapor phase at 150° to 240° C., which is lower than the reaction temperature of the first reactor, in the presence of a fluorinating catalyst. In the third reactor, the unreacted HCC-30 existing in the first reactor is converted into HFC-32 so that the amount of HCC-30 is reduced. Furthermore, the residual CFC-1122 is converted into HCFC-133a so that the amount of CFC-1122 is reduced. HCC-30 may be introduced into the third reactor without introducing into the first reactor, because it is possible to set the reaction condition which is more suitable for the fluorinating reaction of HCC-30 in the third reactor. The reaction temperature of the third reactor is lower by usually from 30° to 170° C., preferably from 50° to 120° C. than the reaction temperature of the first reactor. The reaction pressure is usually from 1 to 20 atm, preferably from 1 to 10 atm. The contact time is usually from 0.5 to 60 seconds, preferably from 2 to 10 seconds. Examples of the fluorinating catalyst are the same as those described in the first reactor. When the reaction temperature is lower than 150° C., a size of the third reactor becomes large. On the other hand, when the reaction temperature is higher than 240° C., CFC-1122 does not react sufficiently.

In a fourth reaction zone having at least one fourth reactor, the reaction mixture obtained from the third reactor is reacted with hydrogen fluoride in a vapor phase at 100° to 190° C., which is lower than the reaction temperature of the third reactor. The reaction temperature of the fourth reactor is lower by usually from 20° to 140° C., preferably from 40° to 70° C., than that of the third reactor. The reaction pressure is usually from 1 to 20 atm, preferably from 1 to 10 atm. The contact time is usually from 0.5 to 60 seconds, preferably from 2 to 10 seconds. When a plurality of fourth reactors exist in the fourth reaction zone, they are connected in a series, and a temperature of a last reactor in this zone which is far from the first reactor is lower than that of a leading reactor in this zone which is near the first reactor. Examples of the fluorinating catalyst are the same as those described in the first reactor. In the fourth reactor, the residual CFC-1122 is converted into HCFC-133a so that the amount of CFC-1122 is reduced. A total volume of the reactor which is required for the reaction of removing CFC-1122 can be reduced by separating into two zones, i.e. third and fourth reactors, in comparison with the case of one zone.

In the fifth reactor, the reaction mixture containing HCFC-133a is reacted with hydrogen fluoride in a vapor phase at a temperature of 170° to 320° C. The reaction temperature of the fifth reactor is usually from 180° to 300° C., preferably from 190° to 280° C. The reaction pressure is usually from 1 to 20 atm, preferably from 1 to 10 atm. The contact time is usually from 0.1 to 30 seconds, pfetefaly from 0.5 to 5 seconds. Examples of the fluorinating catalyst are the same as those described in the first reactor. The presence of HCC-30 and HCC-1120 can give a significant influence on the catalytic life in the second reactor and, therefore, the amount of HCC-30 and HCC-1120 can be decreased in the fifth reactor. Thereby, the catalytic life in the second reactor becomes longer.

In the first to fifth reactors, as a contact system between the catalyst and the raw material, both fluidized and fixed bed types can be used. In addition, a reactor having an insulating type or multi-tube type heating system can be used. In the first reactor, a fixed bed multi-tube type reactor is preferable. The raw material supplied to the first to fifth reactors is preferably introduced into the reactor after previously converting into a gas using an evaporator and the like.

In the method of the present invention, the raw material supplied from the exterior may be HCC-30, HCC-1120 and HF. The supply position of HCC-30 and HCC-1120 supplied from the exterior is not specifically limited. It is preferred to mix the raw material with the reaction mixture fed from the second reactor to the first reactor, or the reaction mixture fed from the first reactor to the third reactor when supplying to the third reactor, because It is effective for the reaction to supply the raw material to the reactor in a state in which the raw material is sufficiently preheated and mixed. As the premixing method, for example, there is a spray-mixing method comprising spraying a cold liquid and mixing it with a heat gas. The supply position of HF supplied from the exterior is not specifically limited, but HF may be supplied in a step of recycling HCFC-133a and HF after removing HFC-32 and HFC-134a. It may also be supplied in several positions, e.g. before the first reactor.

The reaction mixture obtained from the first, third or fourth reactor contains HFC-32, HFC-134a and HCl, and further contain HF, HCFC-133a, HCC-1120, HCC-30, CFC-1122, $CH_2FCl$ (HCFC-31), $CF_2ClCH_2Cl$ (HCFC-132b), etc. It is preferred to remove products (e.g. HFC-32, HFC-134a, HCl, etc.) from the system before feeding to the fifth reactor. The reason why HCl is removed before feeding to the fifth reactor is that the fluorination of HCFC-133a in the fifth and second reactors is prevented by the presence of HCl. These gases can be separated and removed as an liquefied component by the cooling or the cooling under pressure. Since HFC-32, HFC-134a and HCl are contained in the recovered substance wherein the product is removed, these are fed to a fractional distillation column and separated into the above product, the unreacted product and the intermediate raw material. In this case, a separation using a two phase separation may be conducted.

The remainder of the reaction mixture wherein HFC-32, HFC-134a and HCl are removed is optionally separated into a phase which is rich in HCFC-133a and HF and a phase which is rich in HCC-30 and HF by a fractional distillation. It is preferred that the phase which is rich in HCFC-133a and HF is fed to the second reactor and the phase which is rich in HCC-30 and HF is fed to the first reactor so that they are reused.

PREFERRED EMBODIMENT OF THE INVENTION

The following Examples further illustrate the present invention.

COMPARATIVE EXAMPLE 1

The reaction was conducted using a reaction tube (A) (made of Hastelloy C) having a double-tube type heating device and an inner diameter of 25 mm, which was packed with 1500 g of a fluorinating catalyst (chromium oxyfluoride), and a reaction tube (B) packed with 1500 g of a fluorinating catalyst (chromium oxyfluoride).

1,1,1-Trifluorochloroethane (HCFC-133a) and HF in a flow rate (gas flow rate in a standard state, the same in the following) of 28 L/min and 112 L/min, respectively, were introduced into the reaction tube (A) heated to 320° C. and the reaction was conducted to generate 1,1,1,2-tetrafluoroethane (HFC-134a). To the resultant gas, 1,1,2-trichloroethylene (HCC-1120) was added in a flow rate of 4.48 L/min and the reaction was conducted at 240° C. in the reaction tube (B) (made of Hastelloy C) having a double-tube type heating device and an inner diameter of 25 mm, which is packed with 1500 g of a fluorinating catalyst.

The gas evolved from the reaction tube (B) was subjected to GC analysis after deacidificaton. As a result, the efflux rate of HFC-134a was 4.40 L/min, and the conversion of HCC-1120 was 99.2%.

A heat spot at 255° C. was formed at the position which is about 30 cm away from the inlet of an catalyst layer in the reaction tube (B).

Example 1

The same manner as in Comparative Example 1 was repeated except that 1,1,2-trichloroethylene (HCC-1120) was mixed with methylene chloride (HCC-30) having a flow rate of 2.24 L/min and the mixture was introduced into the reaction tube (B).

As a result of the GC analysis, the conversion of HCC-1120 was 98.9% and the efflux rate of HFC-134a was 4.37 L/min. It has been found that the conversion of HCC-1120 and efflux rate of HFC-134a are almost the same as those of Comparative Example 1.

Simultaneously HFC-32 was formed from HCC-30. As a result of the reaction, the conversion of HCC-30 was 92.0% and the selectivity of HFC-32 was 94.4%.

EXAMPLE 2

The same manner as in Example 1 was repeated except that the gas generated in the reaction tube (B) was introduced into the reaction tube (C), which was packed with 1500 g of a fluorinating catalyst (chromium oxyfluoride) and previously heated to 170° C.

As a result of the reaction at the outlet of the reactor (C), the conversion of HCC-30 was 92.1% and the selectivity of HFC-32 was 94.4%, based on the amount of HCC-30 introduced into the reaction tube (B).

At the outlet of the reaction tube (B), CFC-1122 existed in an amount of about 500 ppm based on HFC-134a, but the amount thereof was deceased to 15 ppm at the outlet of the reaction tube (C).

Comparative Example 2

The same manner as in Comparative Example 1 was repeated except that the reaction was conducted by adding 1,1,2-trichloroethylene and methylene chloride in a flow rate of 0.1 L/min and 0.2 L/min, respectively, to an inlet gas of the reaction tube (A).

The efflux rate of HFC-134a from the reaction tube (A) was 4.46 L/min at the beginning of the reaction, but was gradually decreased to 3.35 L/min after 300 hours.

EXAMPLE 3

The same manner as in Comparative Example 2 was repeated except that, after eaeting the above gas In the reaton tube (C) heated previously to 300° C. in which 300 g of a fluorinating catalyst was charged, the reaction gas was further introduced into the reaction tubes (A) and (B) and then reacted.

The gas evolved from the reaction tube (A) was subjected to GC analysis after deacidification. As a result, the efflux rate of HFC-134a from the reaction tube (A) was 4.50 L/min at the beginning of the reaction, and was 4.08 L/min even after 300 hours.

At this time, methylene chloride was hardly detected at the outlet of the reaction tube (C).

EFFECT OF THE INVENTION

The effects of the present invention are as follows.

HCl is generated in the first reactor, and it is supposed that the generated HCl gives a deleterious influence on HFC-134a. In the present invention, however, the practical conversion from HFC-134a into HCFC-133a is smaller than an expected value derived from a relationship of the equilibrium constant and the concentration of the raw material and the generated system. Accordingly, it is possible to produce HCFC-133a and HFC-32 efficiently without causing disadvantageous conversion from HFC-134a into HCFC-133a. The efficiency of energy is good and the formation of a heat spot in the reactor is inhibited.

In the present invention, HCFC-134a and HFC-32 can be produced efficiently. When HFC-134a is used as a diluting agent and excess HF is supplied, HF acts as a heat remover and, therefore, the control of the reaction heat becomes easier and more efficient. In the first reactor, the amount of 1,1-dichloro-2,2-difluoroethylene (CFC-1122) is also reduced.

It as possible to proceed the reaction in the first reactor in the presence of excess HF without causing a problem on the cost of the apparatus and, therefore, the reaction (HCC-30+ 2HF→HFC-32+2HCl) proceeds in good conversion.

According to the present invention, it is possible to give HFC-32 and HFC-134a in good yield without causing a deleterious Influence such as the decrease in conversion of HCC-1120, the decease in amount of HFC-134a, etc.

What is claimed is:

1. A method for producing difluoromethane and 1,1,1,2-tetrafluoroethane, comprising the steps of:
   (1) reacting methylene chloride with hydrogen fluoride in a vapor phase at a reaction temperature of 180° to 320° C. in the presence of a fluorinating catalyst and 1,1,1,2-tetrafluoroethane to give difluoromethane, and reacting 1,1,2-trichloroethylene with hydrogen fluoride to give 1,1,1-trifluorochloroethane, in a first reactor;
   (2) reacting 1,1,1-trifluorochloroethane with hydrogen fluoride in a vapor phase at a reaction temperature of 280° to 400° C., which is higher than the reaction temperature of the first reactor, in the presence of a fluorinating catalyst to give 1,1,1,2-tetrafluoroethane in a second reactor, and supplying the reaction mixture from the second reactor to the first reactor;
   (3) recovering difluoromethane, 1,1,1,2-tetrafluoroethane and hydrogen chloride from the reaction mixture of the first reactor; and
   (4) supplying the remainder of the reaction mixture containing 1,1,1-trifluorochloroethane from the first reactor to the second reactor after recovering in the step (3),
   wherein said fluorinating catalyst is selected from:
   (i) fluorinated chromium oxide obtained by fluorinating a heat-treated hydrate of chromium (III) with hydrogen fluoride,
   (ii) chromium (III) trifluoride,
   (iii) fluorinated aluminum oxide obtained by fluorinating aluminum oxide with hydrogen fluoride, and
   (iv) a catalyst obtained by supporting one element selected from Ti, V, Zr, Mo, Ge, Sn and Pb on alumina, fluorinated alumina or partially fluorinated alumina.

2. The method according to claim 1, wherein methylene chloride and/or chlorofluoromethane existing in the reaction mixture obtained from the first reactor are recovered, and then the recovered methylene chloride and/or chlorofluoromethane are supplied to the first reactor.

3. A method for producing difluoromethane and 1,1,1,2-tetrafluoroethane, comprising the steps of:
   (1) reacting methylene chloride with hydrogen fluoride in a vapor phase at a reaction temperature of 180° to 320° C. in the presence of a fluorinating catalyst and 1,1,1,2-tetrafluoroethane to give difluoromethane, and reacting 1,1,2-trichloroethylene with hydrogen fluoride to give 1,1,1-trifluorochloroethane, in a first reactor;
   (2) reacting 1,1,1-trifluorochloroethane with hydrogen fluoride in a vapor phase at a reaction temperature of 280° to 400° C. in the presence of a fluorinating catalyst to give 1,1,1,2-tetrafluoroethane in a second reactor, and supplying the reaction mixture from the second reactor to the first reactor;
   (3) reacting the reaction mixture from the first reactor with hydrogen fluoride in a vapor phase at a reaction temperature of 150° to 240° C., which is lower than the reaction temperature of the first reactor, in the presence of a fluorinating catalyst to reduce an amount of methylene chloride existing in the reaction mixture, in a third reactor;
   (4) recovering difluoromethane, 1,1,1,2-tetrafluoroethane and hydrogen chloride from the reaction mixture of the third reactor; and
   (5) supplying the remainder of the reaction mixture containing 1,1,1-trifluorochloroethane from the third reactor to the second reactor after recovering in the step (4),
   wherein said fluorinating catalyst is selected from:
   (i) fluorinated chromium oxide obtained by fluorinating a heat-treated hydrate of chromium (III) with hydrogen fluoride,
   (ii) chromium (III) trifluoride,
   (iii) fluorinated aluminum oxide obtained by fluorinating aluminum oxide with hydrogen fluoride, and
   (iv) a catalyst obtained by supporting one element selected from Ti, V, Zr, Mo, Ge, Sn and Pb on alumina, fluorinated alumina or partially fluorinated alumina.

4. The method according to claim 3, wherein methylene chloride and/or chlorofluoromethane existing in the reaction mixture obtained from the third reactor are recovered, and then the recovered methylene chloride and/or chlorofluoromethane are supplied to the first reactor or third reactor.

5. A method for producing difluoromethane and 1,1,1,2-tetrafluoroethane, comprising the steps of:
   (1) reacting methylene chloride with hydrogen fluoride in a vapor phase at a reaction temperature of 180° to 320° C. in the presence of a fluorinating catalyst and 1,1,1,2-tetrafluoroethane to give difluoromethane, and reacting 1,1,2-trichloroethylene with hydrogen fluoride to give 1,1,1-trifluorochloroethane, in a first reactor;
   (2) reacting 1,1,1-trifluorochloroethane with hydrogen fluoride in a vapor phase at a reaction temperature of 280° to 400° C., which is higher than the reaction temperature of the first reactor, in the presence of a fluorinating catalyst to give 1,1,1,2-tetrafluoroethane in a second reactor, and supplying the reaction mixture from the second reactor to the first reactor;
   (3) reacting the reaction mixture from the first reactor with hydrogen fluoride in a vapor phase at a reaction temperature of 150° to 240° C., which is lower than the reaction temperature of the first reactor, in the presence of a fluorinating catalyst to reduce an amount of methylene chloride existing in the reaction mixture, in a third reactor;
   (4) reacting the reaction mixture from the third reactor with hydrogen fluoride in a vapor phase at 100° to 190° C., which is lower than the reaction temperature of the third reactor, in the presence of a fluorinating catalyst, in at least one fourth reactor;
   (5) recovering difluormethane, 1,1,1,2-tetrafluoroethane and hydrogen chloride from the reaction mixture of the fourth reactor; and
   (6) supplying the remainder of the reaction mixture containing 1,1,1-trifluorochloroethane from the fourth reactor to the second reactor after recovering in the step (5),
   wherein said fluorinating catalyst is selected from:
   (i) fluorinated chromium oxide obtained by fluorinating a heat-treated hydrate of chromium (III) with hydrogen fluoride,
   (ii) chromium (III) trifluoride, (iii) fluorinated aluminum oxide obtained by fluorinating aluminum oxide with hydrogen fluoride, and
(iv) a catalyst obtained by supporting one element selected from Ti, V, Zr, Mo, Ge, Sn and Pb on alumina, fluorinated alumina or partially fluorinated alumina.

6. The method according to claim 5, wherein methylene chloride and/or chlorofluoromethane existing in the reaction mixture obtained from the fourth reactor are recovered, and then the recovered methylene chloride and/or chlorofluoromethane are supplied to the first reactor or third reactor.

7. A method for producing difluoromethane and 1,1,1,2-tetrafluoroethane, comprising the steps of:
(1) reacting methylene chloride with hydrogen fluoride in a vapor phase at a reaction temperature of 180° to 320° C. in the presence of a fluorinating catalyst and 1,1,1,2-tetrafluoroethane to give difluoromethane, and reacting 1,1,2-trichloroethylene with hydrogen fluoride to give 1,1,1-trifluorochloroethane, in a first reactor;
(2) reacting 1,1,1-trifluorochloroethane with hydrogen fluoride in a vapor phase at a reaction temperature of 280° to 400° C., which is higher than the reaction temperature of the first reactor, in the presence of a fluorinating catalyst to give 1,1,1,2-tetrafluoroethane in a second reactor, and supplying the reaction mixture from the second reactor to the first reactor;
(3) recovering difluoromethane, 1,1,1,2-tetrafluoroethane and hydrogen chloride from the reaction mixture of the first reactor; and
(4) reacting the remainder of the reaction mixture containing 1,1,1-trifluorochloroethane from the first reactor with hydrogen fluoride in a vapor phase at a temperature of 170° to 320° C. in the presence of a fluorinating catalyst in a fifth reactor after recovering in the step (3), and supplying the reaction mixture from the fifth reactor to the second reactor,
wherein said fluorinating catalyst is selected from:
(i) fluorinated chromium oxide obtained by fluorinating a heat-treated hydrate of chromium (III) with hydrogen fluoride,
(ii) chromium (III) trifluoride,
(iii) fluorinated aluminum oxide obtained by fluorinating aluminum oxide with hydrogen fluoride, and
(iv) a catalyst obtained by supporting one element selected from Ti, V, Zr, Mo, Ge, Sn and Pb on alumina, fluorinated alumina or partially fluorinated alumina.

8. A method for producing difluoromethane and 1,1,1,2-tetrafluoroethane, comprising the steps of:
(1) reacting methylene chloride with hydrogen fluoride in a vapor phase at a reaction temperature of 180° to 320° C. in the presence of a fluorinating catalyst and 1,1,1,2-tetrafluoroethane to give difluoromethane, and reacting 1,1,2-trichloroethylene with hydrogen fluoride to give 1,1,1-trifluorochloroethane, in a first reactor;
(2) reacting 1,1,1-trifluorochloroethane with hydrogen fluoride in a vapor phase at a reaction temperature of 280° to 400° C., which is higher than the reaction temperature of the first reactor, in the presence of a fluorinating catalyst to give 1,1,1,2-tetrafluoroethane in a second reactor, and supplying the reaction mixture from the second reactor to the first reactor;
(3) reacting the reaction mixture from the first reactor with hydrogen fluoride in a vapor phase at 150° to 240° C., which is lower than the reaction temperature of the first reactor, in the presence of a fluorinating catalyst to reduce an amount of methylene chloride existing in the reaction mixture, in a third reactor;
(4) recovering difluormethane, 1,1,1,2-tetrafluoroethane and hydrogen chloride from the reaction mixture of the first reactor; and
(5) reacting the remainder of the reaction mixture containing 1,1,1-trifluorochloroethane from the third reactor with hydrogen fluoride in a vapor phase at a temperature of 170° to 320° C. in the presence of a fluorinating catalyst in a fifth reactor after recovering in the step (4), and supplying the reaction mixture from the fifth reactor to the second reactor,
wherein said fluorinating catalyst is selected from:
(i) fluorinated chromium oxide obtained by fluorinating a heat-treated hydrate of chromium (III) with hydrogen fluoride,
(ii) chromium (III) trifluoride,
(iii) fluorinated aluminum oxide obtained by fluorinating aluminum oxide with hydrogen fluoride, and
(iv) a catalyst obtained by supporting one element selected from Ti, V, Zr, Mo, Ge, Sn and Pb on alumina, fluorinated alumina or partially fluorinated alumina.

9. A method for producing difluoromethane and 1,1,1,2-tetrafluoroethane, comprising the steps of:
(1) reacting methylene chloride with hydrogen fluoride in a vapor phase at a reaction temperature of 180° to 320° C. in the presence of a fluorinating catalyst and 1,1,1,2-tetrafluoroethane to give difluoromethane, and reacting 1,1,2-trichloroethylene with hydrogen fluoride to give 1,1,1-trifluorochloroethane, in a first reactor;
(2) reacting 1,1,1-trifluorochloroethane with hydrogen fluoride in a vapor phase at a reaction temperature of 280° to 400° C., which is higher than the reaction temperature of the first reactor, in the presence of a fluorinating catalyst to give 1,1,1,2-tetrafluoroethane in a second reactor, and supplying the resulting reaction mixture from the second reactor to the first reactor;
(3) reacting the reaction mixture from the first reactor with hydrogen fluoride in a vapor phase at 150° to 240° C., which is lower than the reaction temperature of the first reactor, in the presence of a fluorinating catalyst to reduce an amount of methylene chloride existing in the reaction mixture, in a third reactor;
(4) reacting the reaction mixture from the third reactor with hydrogen fluoride in a vapor phase at 100° to 190° C., which is lower than the reaction temperature of the third reactor, in the presence of a fluorinating catalyst, in at least one fourth reactor;
(5) recovering difluoromethane, 1,1,1,2-tetrafluoroethane and hydrogen chloride from the reaction mixture of the fourth reactor; and
(6) reacting the remainder of the reaction mixture containing 1,1,1-trifluorochloroethane from the fourth reactor with hydrogen fluoride in a vapor phase at a temperature of 170° to 320° C. in the presence of a fluorinating catalyst in a fifth reactor after recovering in the step (5), and supplying the reaction mixture from the fifth reactor to the second reactor;
wherein said fluorinating catalyst is selected from:
(i) fluorinated chromium oxide obtained by fluorinating a heat-treated hydrate of chromium (III) with hydrogen fluoride,
(ii) chromium (III) trifluoride,
(iii) fluorinated aluminum oxide obtained by fluorinating aluminum oxide with hydrogen fluoride, and
(iv) a catalyst obtained by supporting one element selected from Ti, V, Zr, Mo, Ge, Sn and Pb on alumina, fluorinated alumina or partially fluorinated alumina.

10. The method according to claim 3, 5, 8 or 9, wherein methylene chloride is reacted with hydrogen fluoride in the third reactor instead of the first reactor.

11. The method according to claim 3, wherein methylene chloride is reacted with hydrogen fluoride in the third reactor instead of the first reactor, and methylene chloride and/or chlorofluoromethane existing in the reaction mixture obtained from the third reactor are recovered, and then the recovered methylene chloride and/or chlorofluoromethane are supplied to the third reactor.

12. The method according to claim 5, wherein methylene chloride is reacted with hydrogen fluoride in the third reactor instead of the first reactor, and methylene chloride andlor chlorofluoromethane existing in the reaction mixture obtained from the fourth reactor are recovered, and then the recovered methylene chloride and/or chlorofluoromethane are supplied to the third reactor.

13. The method according to claim 1, wherein a mole amount of hydrogen fluoride in the first reactor is from 1 to 50 times, based on the total value of a 3-fold value of the mole amount of 1,1,2-trichloroethylene and 2-fold value of mole amount of methylene chloride.

14. The method according to any claim 1, wherein a mole amount of hydrogen fluoride in the first reactor is from 10 to 20 times, based on the total value of a 3-fold value of the mole amount of 1,1,2-trichloroethylene and 2-fold value of mole amount of methylene chloride.

* * * * *